US00PP08438P

United States Patent [19]

Cobia et al.

[11] Patent Number: Plant 8,438

[45] Date of Patent: Oct. 26, 1993

[54] CACTACEAE PLANT NAMED 'PASADENA'

[76] Inventors: Barnell L. Cobia; Mark E. Cobia, both of P.O. Box 771369, Winter Garden, Fla. 34777-1369

[21] Appl. No.: 933,926

[22] Filed: Aug. 24, 1992

[51] Int. Cl.[5] ..... A01H 5/00

[52] U.S. Cl. ..... Plt./88.5

[58] Field of Search ..... Plt./88.5

[56] References Cited

U.S. PATENT DOCUMENTS

P.P. 3,688 3/1975 Cobia et al. ..... Plt. 88

*Primary Examiner*—James R. Feyrer

*Assistant Examiner*—Elizabeth C. Kemmerer

*Attorney, Agent, or Firm*—Roger L. Martin

[57] ABSTRACT

A new and distinct plant variety of the Cactaceae family is of the type known commercially as a 'Christmas Cactus' and has a growth habit which is similar to that of the 'Kris Kringle' variety (U.S. Plant Pat. No. 3,688) but which, nevertheless, differs, among other things, by having phylloclades with thicker midribs, wider and thicker wings, longer teeth in greater number per phylloclade, and sterile flowers with wider tube laminating and tube forming tepals, fewer tube attached stamen that are greater in length, a stamen that is greater in length, and an ovary with longer major and minor axis.

3 Drawing Sheets

BACKGROUND OF THE INVENTION

The invention relates to a new and distinct plant variety of the Cactaceae family and which has been named the *Zygocactus truncatus* 'Pasadena' by the inventor.

Certain plant varieties of the Cactaceae family are well known in the foliage plant market and among these are those which are commonly referred to as the Christmas Cactus varieties because they tend to bloom during the Thanksgiving-Christmas holiday season in the northern hemisphere.

The Christmas Cactus varieties on the market have blooms which vary in color from one variety to the next as is evident from the current U.S. patent art. One of the more popular varieties sold commercially in the market place is the variety that has been named *Zygocactus truncatus* 'Kris Kingle'. The variety has a red colored bloom and forms the subject matter of U.S. Plant Pat. No. 3,688.

SUMMARY OF THE INVENTION

A general objective has been to develop a new plant variety with a red colored bloom and which is distinguishable from the 'Kris Kringle' variety and capable of being marketed in competition therewith. The objective has been fully realized in the development of the new plant variety hereinafter described in detail. The new plant variety was developed in a nursery located at Winter Garden, Fla., from a mutation that appeared on a specimen of an unnamed research variety designated ZH11039, which was under cultivation at the nursery.

Through successive propagation of cuttings taken from the mutated plant part, it has been ascertained that specimens of the new plant variety generally resemble the 'Kris Kringle' variety in most respects but are distinguishable from this variety and from other related varieties known to the inventors by a growth habit which is evident in plant specimens of the new plant variety that have been propagated and grown under nursery conditions utilized in the growing of tropical plants in Winter Garden, Fla., as combining the following principal characteristics:

1. An erect growth habit,
2. Phylloclades which, in comparison to the 'Kris Kringle' variety, have (a) midribs with generally greater thickness dimensions, (b) wings with generally greater thickness and width dimensions, and (c) teeth with generally greater length dimensions and in larger number per phylloclade.
3. Flowers which, in comparison to the 'Kris Kringle' variety, are sterile and have (a) a tube laminating tepal series with generally greater width dimensions, (b) a perianth tube that at the throat has a generally longer major axis, (c) a tube forming series of tepals with generally greater width dimensions, (d) a tube attached group of stamens that are generally fewer in number and generally greater in length dimensions, (e) a style that is generally greater in length dimensions, and (f) an ovary that at the major and minor axis is generally greater in length.

BRIEF DESCRIPTION OF THE DRAWINGS

The accompanying drawings serve by color photographic means to illustrate the new plant variety and wherein one sheet shows a (6) month old specimen which was grown from the propagation of a single phylloclade in a conventional 3.5" plastic pot (trade designated size) found in the marketplace.

A second sheet shows an enlargement of a fully open bloom taken from the specimen shown in the first mentioned sheet.

Still another sheet shows a bloom as sectioned generally longitudinally through the perianth tube and ovary to expose the style and stamen arrangement.

DETAILED PLANT DESCRIPTION

The following is a detailed description of the new plant variety with colors and hues, unless otherwise clearly indicated by the text, as for example, through the absence of color notations, being named in accord with the ISCC-NBS Method for Designating Colors (U.S. Department of Commerce, National Bureau of Standards, Circular 553), the named colors being interpreted from color notations derived by comparison with color specimens of the Munsell Book of Color.

The description is further based on observations of well fertilized plants about one year old from initial propagation of a single phylloclade and which were grown under 50-75% shaded glass house nursery conditions in the Winter Garden, Fla. area and wherein temperatures range from 60°-85° F. during the winter months, from 75°-95° during the summer months, and are ambient during the intervening periods.

I. Name: *Zygocactus truncatus* 'Pasadena '.

II. Parentage: This variety was developed from a mutation that occurred on a plant specimen of an unnamed and unmarketed research variety designated as ZH11039.

III. Classification:

A. *Botanic* (*Britton and Rose, The Cactaceae, Constable and Co., Ltd., London* 1937, *Vol. IV*).—(1) Family: Cactaceae. (2) Tribe: Cereeae. (3) Sub-Tribe: Epiphyllanae. (4) Genus: Zygocactus. (5) Species: *truncatus* (Haworth) Schumann.

B. *Commercial.*—Thanksgiving-Christmas blooming cactus.

IV. Form: Epiphylic and terrestrial, shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pith surrounding vascular bundles of the vascular system to the marginal teeth. (b) Texture — Smooth, waxy epidermis with wax in small embedded scales and becoming woody in basal stem areas with specimen aging. (c) Size (at maturity) — 1. Length: Usually 31-51 mm. (Avg.=40.3 mm.) (Dev.=5.05 mm.) 2. Thickness: Usually 3-9 mm. (Avg.=4.9 mm.) (Dev.=1.62 mm.) (d) Color (at maturity) — Usually dominated by a yellow green and/or olive green hue. Commonly moderate yellow green (5 GY 5/6) (7.5 GY 5/6) and/or moderate olive green (7.5 GY 4/6). (3) Wings: (a) General — Dentate and generally flattened from midrib cortex to tooth insertion and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with specimen aging. (d) Size (at maturity) — 1. Thickness: About 1.5-3.0 mm. in the area intermediate the margin and midrib. (Avg.=2.3 mm.) (Dev.=0.40 mm.) 2. Width — Usually 12-19 mm. as measured from phylloclade axis to most offset lateral aerole. (Avg.=15.9 mm.) (Dev.=2.14) 3. Color (at maturity) — Usually dominated by an olive green hue. Commonly moderate olive green (7.5 GY 4/6) (7.5 GY 4/4). 4. Teeth: (a) Shape — 1. General: Generally flattened and tapered along the margins and from the wing insertion to an apex having a hyaline, single cell, pointed spine with nonpredictable bending. 2. Abaxial margin: Usually straight to convex. 3. Adaxial margin: Usually straight to concave. (b) Orientation — Generally project distally of phylloclade in an alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Usually 1-2 mm. in center area. (Avg.=1.5 mm.) (Dev.=0.36 mm.) 2. Areole to apex dimension (adaxial marginal side): Usually 6-13 mm. in the upper quadrants of the phylloclades. (Avg.=9.2 mm.) (Dev.=1.90 mm.) (f) Number — Usually 8-12 per phylloclade. (g) Color — Usually dominated by an olive green hue. Commonly moderate olive green (7.5 GY 4/4) (7.5 GY 3/4). (5)Areoles: (a) Terminal areole — Large, elongated, oval shaped with several acicular bristles, and several buds that may mature into either new phylloclades or flowers. The opposite ends of the areole are located adjacent to subsidiary areoles which are in turn located at the axil of the teeth at the distal end of the phylloclade. (b) Axillary areoles — Acicular bristles without glochidia but having copious, short, brownish, multicellular, wooly hairs. In areoles located below the teeth at the distal end of the phylloclade, there is usually only one areole which is frequently latent.

VI. Buds: Unarmored, ovoid and chlorophyllous.

VII. Flowers:

A. *General.*—Sessile, zygomorphic, usually solitary, terminal, perfect and epigynous with double hypanthium and whorled tepals (undifferentiated sepals and petals) having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 5-6. (5) Size (at full bloom): (a) Length (base-tip dimension) — Usually less than 21 mm. (Avg.=11.4 mm.) (Dev.=5.23) (b) Width (maximum) — Usually less than 14 mm. (Avg.=9.7) (Dev.=2.38) (6) Color (at full bloom): Varies from the outer members to the inner members with the smallest outer whorl tepals usually having a marginal blade area that in color is dominated by a yellowish pink, pink, and/or red hue, and a center field area that is dominated by a yellow green hue. The inner whorl tepal members have marginal and center blade areas that in color are usually dominated by red hues that project proximally into a basal area that is dominated by a yellow green hue. Commonly moderate red (5 R 5/10), strong red (5 R 5/12), and/or vivid red (5 R 4/14) in marginal and center field areas of inner whorl members and pale yellow green (5 GY 9/2) and/or light yellow green (5 GY 9/4) in the basal area. Commonly deep pink (5 R 6/10), moderate red (5 R 5/10), strong red (5 R 5/12), and/or strong yellowish pink (5 R 7/8) in marginal areas and merging with a center field and basal area that is commonly strong yellow green (5 GY 7/10) (5 GY 6/8) (2.5 GY 6/8) (2.5 GY 7/8) in the outer whorl members. (7) Orientation: Erect to recurve at full bloom.

C. *Tube laminating series.*—(1) General: Tepals inserted on ovary and basally united below the throat as outer lamination on the perianth tube and with progressively greater amount of basal fusion inwardly in the whorl. (2) Shape: Zygomorphic and grading inwardly in the whorl with progressively greater length dimensions and broader apices so that the blade area changes inwardly in the whorl from ovate with an acute tip to spatulate with a rounded to obtuse tip. Entire margins with sparse, irregular teeth mainly in apex areas. (3) Texture: Succulent and glabrous outer whorl members and grading inwardly to silken blades with slightly fleshy basal areas. (4) Number: Usually 5–8 tepals. (5) Size: (at full bloom): (a) Length (base-tip dimension) — usually ranging from about 22 to about 59 mm. (Avg.=3.6 mm.) (Dev.=10.73 mm.) (b) Width (maximum) — Usually ranging from about 14 to about 24 mm. (Avg.=18.4 mm.) (Dev.=1.98 mm.) (6) Color (at full bloom): (a) General — Tepals with a basal area that are usually dominated by a greenish white and/or yellow green hue immediately above the insertion on the outer members and becoming white, pinkish white and/or pale pink inwardly in the whorl. Marginal blade and blade center field areas that in color are dominated by a red hue which merges with the distally extending basal area colors. (b) Basal area — Inner members commonly white (2.5 R 9/0), pinkish white (5 R 9/1), and/or pale pink (5 R 9/2) along tube attached areas. Outer members commonly greenish white (5 GY 9/1) and/or pale yellow green (5 GY 9/2). (c) Blade area — Commonly strong red (5 R 5/12) and/or vivid red (5 R 4/14). (7) Orientation: Perpendicular to recurve at full bloom.

D. *Tube forming series.*—(1) General: Tepals basally united to form hollow perianth tube that is inserted on ovary and equipped at its throat with an irregular carina (keel). (2) Shape: (a) Perianth tube — Elongated and elipsoidal in cross section with the major ellipsoidal axis usually generally normal to the plane of the supporting phylloclade. (b) Blades — Nearly zygomorphic and thinly spatulate with rounded tips and entire margins having sparse irregular teeth in apex area. (c) Carina (keel) — Irregular and transcending. (3) Texture: (a) Perianth Tube — Thick, succulent and slightly ribbed. (b) Blades — Translucent and silken. (c) Carina (keel) — Fleshy. (4) Number: Usually 8–9. (5) Size (at full bloom): (a) Perianth tube — 1. Length (base-keel): Usually 32–37 mm. along tube axis. (Avg.=34.1 mm.) (Dev.=1.58) 2. Major Axis: Usually 13–15 mm. at throat interior. (Avg.=13.9 mm.) (Dev. 0.78 mm.) 3. Minor Axis: Usually 8–9 mm. at throat interior. (Avg.=8.7 mm.) (Dev.=0.48 mm.) (b) Blades — 1. Length (keel - tip): Usually 30–34 mm. (Avg.=32.4 mm.) (Dev.=1.09 mm.) 2. Width (maximum): Usually 15–22 mm. (Avg.=18.1 mm.) (Dev.=1.53 mm.) (6) Color (at full bloom): (a) Perianth Tube — A basic field that is generally translucent and white with longitudinally extending, randomly arranged striations or streaks that in color are commonly pinkish white (5 R 9/1) and/or pale pink (5 R 9/2). The basic field is translucent and commonly white (2.5 R 9/0). (b) Blades — A continuous marginal and center blade area distally of the keel that in color is dominated by a red hue and which merges with a basal area distally of the keel that is usually translucent and white. Commonly strong red (5 R 5/12) and/or vivid red (5 R 4/14) in the continuous marginal and center blade areas of the blade. Commonly pinkish white (5 R 9/1), pale pink (5 R 9/2), and/or white (2.5 R 9/0) in the basal area distally of the keel. (c) Carina (keel) — Color usually dominated by a purplish pink hue. Commonly deep purplish pink (5 RP 6/10) (2.5 RP 6/10). (7) Orientation: Acute to recurve with revolute tendencies.

E. *Androecium (stamens).*—(1) General: Numerous exerted and diadelphous stamens with one group having filaments basally fused to the perianth tube and the other group having filaments basally united to form a nectary housing, thin annulus around the style and which is provided with thin, deflexed, irregular, toothed margin or ruffle at the throat of the annulus. (2) Stamen number: (a) Tube attached group — Usually 47–72. (b) Basally united group — Usually 18–22. (3) Filaments: (a) General — Translucent with anther connective. (b) Shape — Long, slender, terete. (c) Texture — Glabrous and capillaceous. (d) Color — Commonly white (2.5 R 9/0) (2.5 R 9.5/0) over entire length. (e) Size (at full bloom) — 1. Length: a. Tube attached group — Usually 34–64 mm. (Avg.=5.27 mm.) (Dev.=7.58 mm.) b. Basally united group — Usually 40–55 mm. (Avg.=47.0 mm.) (Dev.=4.52 mm.) 2. Diameter: Usually about 0.25–0.50 mm. intermediate opposite ends. (4) Anthers: (a) General — Adnate with four longitudinally dehiscent pollen sacs and connective inserted at end. (b) Shape — Elongated. (c) Texture — Waxy. (d) Color (before dehiscence) — Dominated by a yellow hue. Commonly pale yellow (5 Y 9/4) and/or light yellow (5 Y 9/6). (e) Sterility — Sterile.

F. *Gynoecium (pistil).*—(1) General: Exerted and compound, parietal placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Usually dominated by a purplish red hue at the basal end of the style and progressively varying to a color dominated by a purplish red, reddish purple, and/or purplish pink hue at the distal end. Commonly moderate purlish red (5 RP 5/10) at the basal end and moderate purplish red (5 RP 5/10), deep purplish pink (5 RP 6/10), and/or strong reddish purple (2.5 RP 5/10) at the distal end. (e) Size (at full bloom) — 1. Length: Usually 59–71 mm. (Avg.=65.1 mm.) (Dev.=3.78 mm.) 2. Diameter: Usually 1.0–1.5 mm. intermediate opposite ends. (3) Stigma: (a) General — Exerted and erect with usually 5–7 inner marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Usually dominated by a reddish purple and/or purplish pink hue. Commonly light reddish purple (2.5 RP 6/8) and/or deep purplish pink (5 RP 6/10). (e) Size — 1. Length: Usually 4–6 mm. along inner margins. (4) Ovary: (a) General — Inferior with thin epidermis and usually 4–5 carpels with numerous ovules. (b) Shape — Terete to ovoid and generally broadening from insertion to floral end. (c) Texture — Succulent with glabrous thin outer epidermis. (d) Color — A basic field with color usually dominated by a yellow green hue. Commonly moderate yellow green (2.5 GY 6/6) (2.5 GY 5/6) and/or strong yellow green (2.5 GY 6.8). (e) Size — 1. Length: Usually 8–10 mm. from insertion to cavity base. (Avg.=9.0 mm.) (Dev.=0.71 mm.) 2. Major axis: Usually 10–12 mm. at distal end of concavity. (Avg.=11.2 mm.) (Dev.=0.80 mm.) 3. Minor axis: Usually 9–11 mm. at distal end of concavity. (Avg.=10.0 mm.) (Dev.=0.71 mm.)

VIII. Growth habit: Erect.

General Description of a Plant Specimen

Age of plant: Six (6) months from initial propagation of single phylloclade.

Branches from propagated phylloclade: One (1).

Total number of new phyllocaldes grown: Eight (8).

General:

| GENERAL: Branch Number | Number of Phylloclades | Maximum Length | Number of Tips |
|---|---|---|---|
| 1 | 8 | 51 mm. | 3 |

| MIDRIBS: Branch Number | Average Midrib Length | Average Midrib Thickness |
|---|---|---|
| 1 | 45.6 mm. | 5.1 mm. |

| WINGS: Branch Number | Average Wing Center Thickness | Average Wing Width (Maximum) |
|---|---|---|
| 1 | 2.1 mm. | 17.3 mm. |

| TEETH: Branch Number | Teeth (Avg.) Per Phylloclade | Average Tooth Center Thickness | Average Areole To Apex Length |
|---|---|---|---|
| 1 | 10.0 | 1.4 mm. | 8 · 5 |

Phylloclade color: moderate yellow green (5 GY 5/6) (7.5 GY 5/6) and moderate olive green (7.5 GY 4/6) (7.5 GY 4/4) (7.5 GY 3/4).

GENERAL DESCRIPTION OF A FLOWER

The following is a general description of a flower of the new plant variety and which bloomed in December on a 6 month old plant specimen grown under shaded greenhouse nursery conditions in Winter Garden, Fla.

Number of buds and blooms on plant specimen: 3.

Bloom life: 8 days.

Sepaloid series of tepals:

*Number.*—6.

*Tepal size (at full bloom).*—Maximum base-tip dimension: 19 mm. Minimum base-tip dimension: 7 mm. Maximum width dimension: 12 mm.

*Color (at full bloom).*—Moderate red (5 R 5/10) and strong red (5 R 5/12) in marginal and center field area of inner whorl members and pale yellow green (5 GY 9/2) and light yellow green (5 Gy 9/4) in the basal areas. Deep pink (5 R 6/10), moderate red (5 R 5/10), and strong red (5 R 5/12) in marginal areas and merging with a center field and basal area that is strong yellow green (5 GY 7/10) (2.5 GY 6/8) (5GY 6/8) in the outer members.

Tube laminating series of tepals:

*Number.*—8.

*Size (at full bloom).*—Maximum base-tip dimension: 57 mm. Minimum base-tip dimension: 22 mm. Maximum blade width: 23 mm. Minimum blade width: 18 mm.

*Color (at full bloom).*—Inner members white (2.5 R 9/0) and pinkish white (5 R 9/1) with outer members being greenish white (5 GY 9/1) along tube attached areas. Strong red (5 R 5/12) and vivid red (5 R 4/14) in the blade and center field areas.

Tube forming series of tepals:

*Number.*—8.

*Size (at full bloom).*—Perianth tube: Length (base to keel) — 35 mm. along the tube axis Major axis — 14 mm. at throat interior. Minor axis — 8 mm. at throat interior. Blades: Maximum length (keel-tip) — 33 mm. Minimum lenth (keel-tip) — 31 mm. Maximum blade width — 20 mm. Minimum blade width — 18 mm.

*Color.*—Perianth tube: A basic field that is generally translucent and white (2.5 R 9/0) with random striations of pinkish white (5 R 9/1) and pale pink (5 R 9/2). Blades: Strong red (5 R 5/12) and vivid red (5 R 4/14) in the continuous marginal and center blade areas of the blade. Pinkish white (5 R 9/1) and white (5 R 9/0) in the basal area distally of the keel.

Androecium:

*Stamen number.*—Tube attached group: 64. Basally united group: 21.

*Filaments.*—Color: White (2.5 R 9/0) (2.5 R 9.5/0).

*Size (at full bloom).*—Length — Tube attached group: 55 mm. (avg). Basally united group: 48 mm. (avg). Diameter: About 0.25 mm. intermediate the opposite ends.

*Anthers.*—Color (before dehiscing): Pale yellow (5 Y 9/4) and light yellow (5 Y 9/6).

Gynoecium (pistil):

*Style.*—Color: Moderate purplish red (5 RP 5/10) in basal area and moderate purplish red (5 RP 5/10), deep purplish pink (5 RP 6/10), and strong reddish purple (2.5 RP 5/10 ) in distal area. Size (at full bloom): Length — 68 mm. Diameter — 1.5 mm. Stigma — Color: Light reddish purple (2.5 RP 6/8) and deep purplish pink (5 RP 6/10). Size: 6 mm. (avg) lobe length.

Ovary — Color: moderate yellow green (2.5 GY 6/6) (2.5 GY 5/6), and strong yellow green (2.5 GY 6/8). Size (at full bloom): Length (insertion to concavity base) — 10 mm. Major axis — 11 mm. at distal end of concavity. Minor axis — 10 mm. at distal end of concavity.

We claim:

1. A new and distinct plant variety of the Cactaceae family as shown and described and which is mainly distinguished from its antecedents and known related varieties by growth characteristics that are similar to those of the 'Kris Kringle ' variety but as modified by the combination of the following characteristics:

1. a more erect posture at maturity than the 'Kris Kringle' variety;

2. phylloclades which, in comparison to the 'Kris Kringle' variety have (a) midribs with generally greater thickness dimensions, (b) wings with generally greater thickness and width dimensions, and (c) teeth with generally greater length dimensions and in larger number per phylloclade;
3. flowers which, in comparison to the 'Kris Kringle' variety, have (a) a tube laminating tepal series with generally greater width dimensions, (b) a perianth tube that at the throat has a generally longer major axis, (c) a tube forming series of tepals with generally greater width dimensions, (d) a tube attached group of stamens that are generally fewer in number and generally greater in length dimensions, and (f) an ovary that at the major and minor axis is generally greater in length.

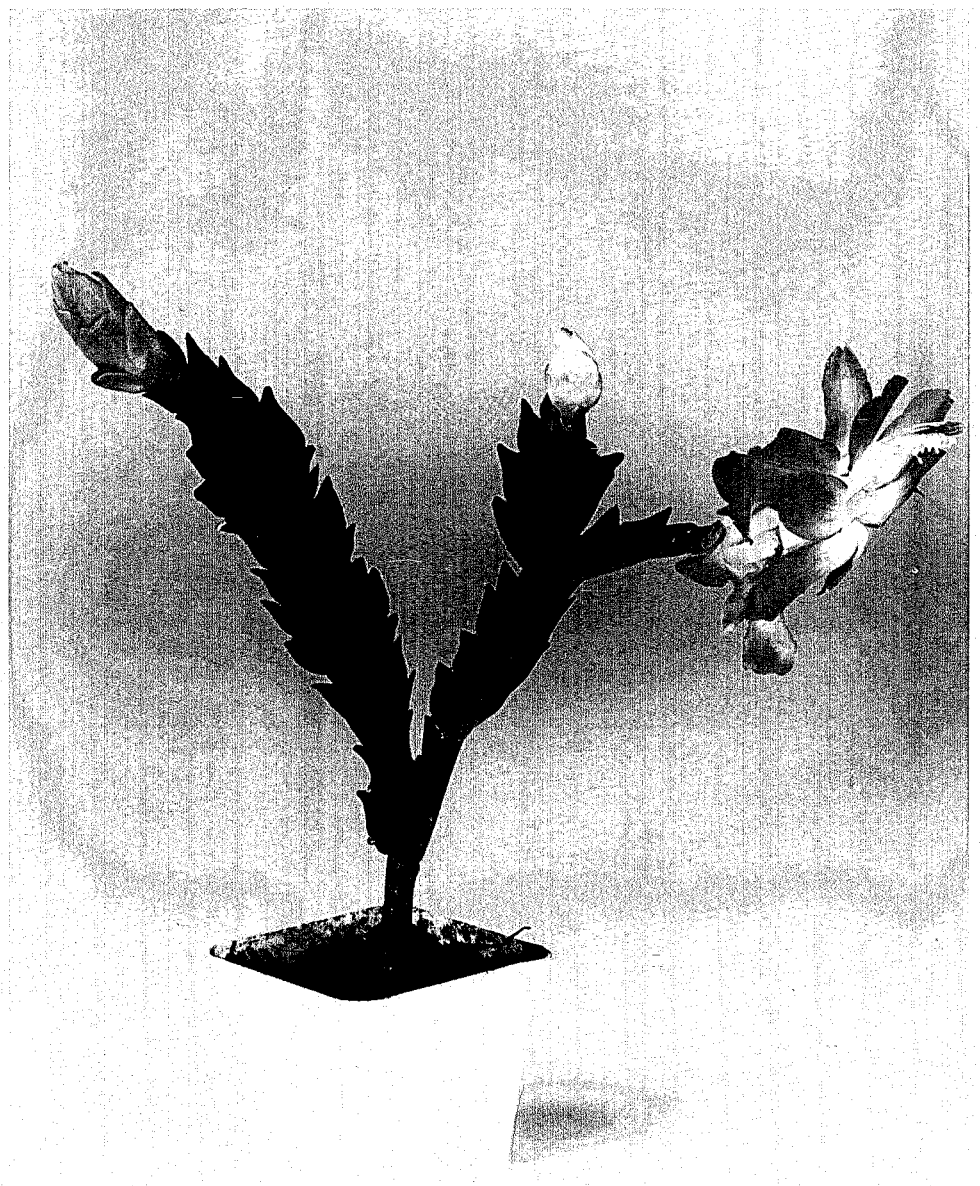

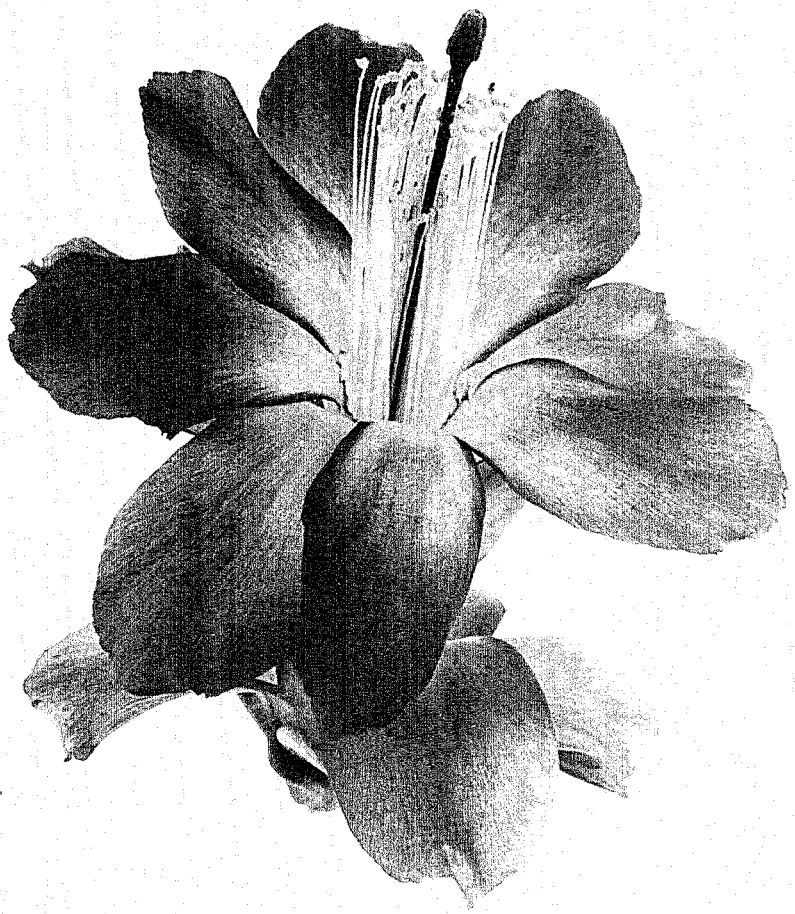

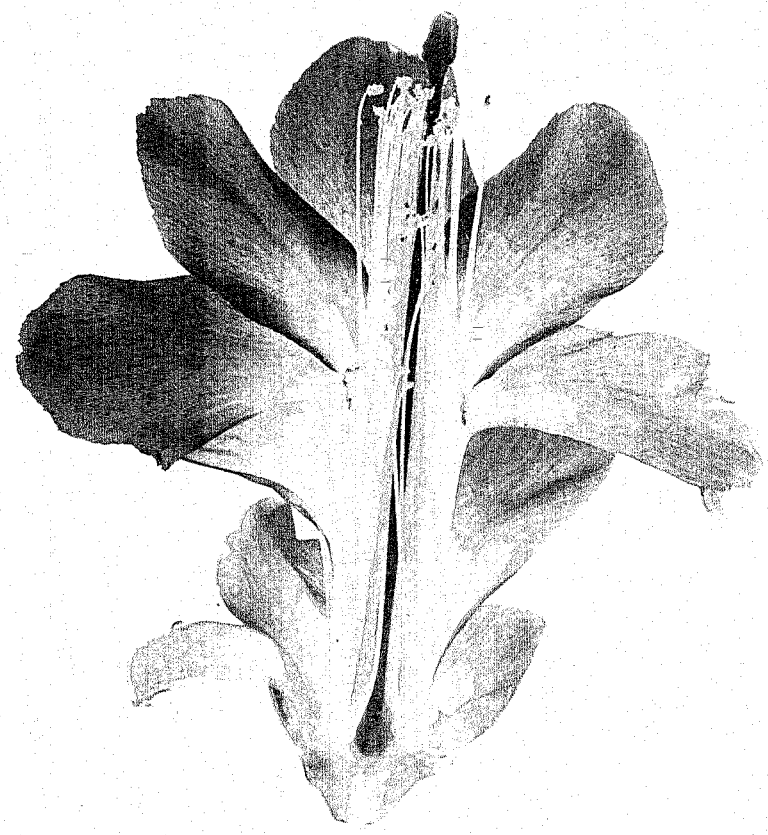

* * * * *